Figure 1A:
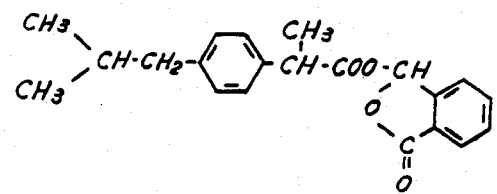
Figure 1A:
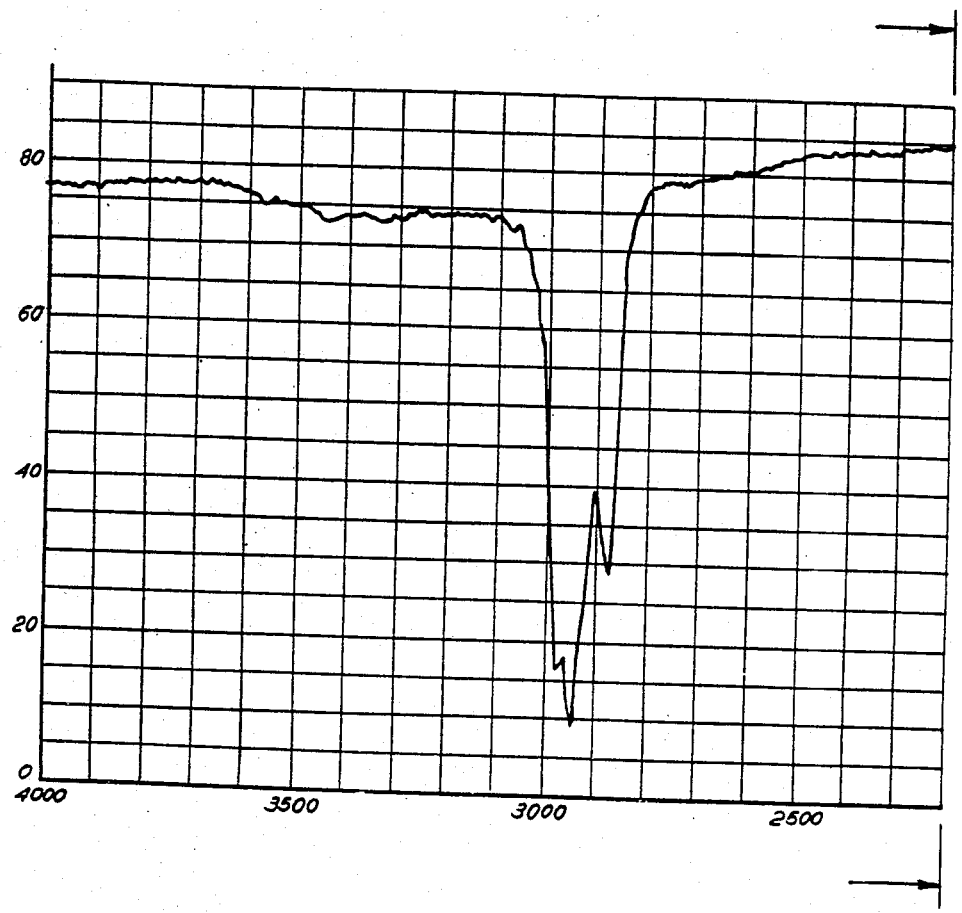

United States Patent [19]

Vandoni et al.

[11] Patent Number: 4,529,737

[45] Date of Patent: Jul. 16, 1985

[54] ANALGESIC AND ANTI-INFLAMMATORY ARYLALKANOIC ACID PHTHALIDYL ESTERS AND PHARMACEUTICAL COMPOSITIONS THEREOF

[75] Inventors: Guido Vandoni; Marino Gobetti, both of Milan, Italy

[73] Assignee: Resfar S.r.I., Italy

[21] Appl. No.: 206,454

[22] Filed: Nov. 13, 1980

[30] Foreign Application Priority Data

Nov. 23, 1979 [IT] Italy ............................. 27539 A/79

[51] Int. Cl.³ ................. C07D 307/88; A61K 31/365
[52] U.S. Cl. .................................... 514/470; 549/305
[58] Field of Search .......................... 424/279; 549/305

[56] References Cited

FOREIGN PATENT DOCUMENTS

| 858897 | 1/1978 | Belgium . |
| 1450043 | 8/1973 | United Kingdom . |
| 2016001 | 9/1979 | United Kingdom . |
| 1553171 | 9/1979 | United Kingdom . |

*Primary Examiner*—Jane T. Fan
*Attorney, Agent, or Firm*—Ostrolenk Faber Gerb & Soffen

[57] ABSTRACT

The present invention concerns novel phthalidyl esters of arylalkanoic acids having improved pharmacological properties in respect to the corresponding arylalkanoic acids having analgesic and anti-inflammatory activity, as well as pharmaceutical compositions containing them as active ingredients. The invention further relates to a method for improving the pharmacological properties of said arylalkanoic acids having analgesic and anti-inflammatory activity, by introducing, through an ester bond, a phthalidyl group.

12 Claims, 6 Drawing Figures

ANALGESIC AND ANTI-INFLAMMATORY ARYLALKANOIC ACID PHTHALIDYL ESTERS AND PHARMACEUTICAL COMPOSITIONS THEREOF

DESCRIPTION

The present invention concerns new arylalkanoic acids phtalidyl esters having improved pharmacological properties with respect to the corresponding arylalkanoic acids having analgesic and anti-inflammatory activity, as well as pharmaceutical compositions containing them as active ingredients and a method for improving the pharmacological characteristics of the arylalkanoic acids having analgesic and anti-inflammatory activity.

The term "arylalkanoic acids having analgesic and anti-inflammatory activity" as used herein, indicates the acetic, propionic and butyric acids unsubstituted in the alkane chain or substituted in said alkane chain by a chlorine atom or by a hydroxy, methoxy or oxo group and bearing on said alkane chain a substituted or unsubstituted biphenylyl, naphthyl, or phenyl group or a benzene ring being included in a fused ring heterocyclic moiety, which are known as analgesic and anti-inflammatory agents.

It is known that the above mentioned arylalkanoic acids having analgesic and anti-inflammatory activity are useful and have been widely used for the treatment of rheumatoid arthritis and of other degenerative conditions with a phlogistic component of the locomotor apparatus. However, said arylalkanoic acids having analgesic and anti-inflammatory activity present some disadvantages deriving, in general, from their acidity and from their not negligible toxicity.

The chemical and pharmacological researchers have been working for many years in order to find new compounds which, besides having an activity equal to or higher than that of the known products, exhibit less side effects. It has now been found that by introducing a phthalidyl group, through an ester bond, into the molecule of the arylalkanoic acids having analgesic and anti-inflammatory activity, new phthalidyl esters of said arylalkanoic acids having analgesic and anti-inflammatory activity are obtained, in which the above mentioned disadvantages of said arylalkanoic acids having analgesic and anti-inflammatory activity are greatly reduced and even eliminated and their pharmacological activity is in general enhanced.

Thus, it is an object of the present invention to provide new phthalidyl esters of arylalkanoic acids having analgesic and anti-inflammatory activity which have reduced or negligible side effects and, in general, an enhanced pharmacological activity with respect to the corresponding free acids.

According to a preferred embodiment, the present invention provides new chemical compounds characterized by the following general formula:

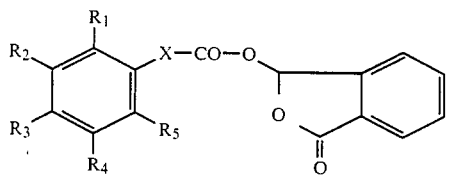

I wherein $R_1$ is hydrogen; $R_2$ is hydrogen, $R_3$ is hydrogen, alkyl having 1 to 5 carbon atoms, cyclopentyl, cyclohexyl, 3-oxo-cyclohexyl and its oxime, 1-cyclohexenyl, 3-oxo-1-cyclohexenyl, lower alkoxy having from 1 to 5 carbon atoms, lower alkenyloxy having 3 or 4 carbon atoms, cyclopropylmethoxy, cyclopropylcarbonyl, phenyl, fluorophenyl, 1-oxo-2-isoindolinyl, 2,5-dihydro-1H-1-pyrrolyl or 2-thenoyl; $R_4$ is hydrogen, fluorine, chlorine, phenoxy, benzoyl or chloro-benzoyl; $R_5$ is hydrogen, amino, 2,4-dichlorophenoxy or the 2,6-dichloroanilino group; $R_3$ and $R_2$ can be joined by a $-CH=CH-C(OCH_3)=CH-$ grouping and X is a $-CH(Cl)-$, $-CH(CH_3)-$, $-CH_2-$ or $COCH_2CH_2-$ group; provided that one of $R_1$, $R_2$, $R_3$, $R_4$ and $R_5$ is other than hydrogen and at least three of them must be hydrogen, and when $R_2$ is joined to $R_3$ by a $-CH=CH-C(OCH_3)=CH-$ grouping X is only a $-CH(CH_3)-$ group, and when $R_3$ is other than hydrogen, $R_1$, $R_2$ and $R_5$ are hydrogen and $R_4$ is other than phenoxy, benzoyl or chlorobenzoyl, and when $R_4$ is phenoxy, benzoyl or chlorobenzoyl, $R_1$, $R_2$ and $R_3$ are hydrogen, and $R_5$ is other than 2,6-dichloroanilino and 2,4-dichlorophenoxy, when $R_5$ is 2,6-dichloroanilino or 2,4-dichlorophenoxy, $R_1$, $R_2$, $R_3$ and $R_4$ are all hydrogen.

Exemplary phthalidyl esters of arylalkanoic acids having analgesic and anti-inflammatory activity according to the present invention included in formula I above are the phthalidyl esters of the compounds hereinbelow indicated by their International Non-proprietary Name (INN) and/or by their chemical name:

ibufenac (INN) $R_1=R_2=R_4=R_5=H$; $X=CH_2$, $R_3=$isobutyl;

ibuprofen (INN) $R_1=R_2=R_4=R_5=H$; $X=CH(CH_3)$; $R_3=$isobutyl flurbiprofen (INN) $R_1=R_2=R_5=H$; $X=CH(CH_3)$; $R_3=$phenyl; $R_4=F$ hexaprofen (INN) $R_1=R_2=R_4=R_5=H$; $X=CH(CH_3)$; $R_3=$cyclohexyl;

indoprofen (INN) $R_1=R_2=R_4=R_5=H$; $X=CH(CH_3)$; $R_3=$1-oxo-2-isoindolinyl;

diclofenac (INN) $R_1=R_2=R_3=R_4=H$; $X=CH_2$; $R_5=$2,6-dichloroanilino;

pirprofen (INN) $R_1=R_2=R_5=H$; $X=CH(CH_3)$; $R_3=$2,5-dihydro-1H-1-pyrrolyl; $R_4=Cl$ tetriprofen (INN) $R_1=R_2=R_4=R_5$; $X=CH(CH_3)$; $R_3=$1-cyclohexenyl;

alclofenac (INN) $R_1=R_2=R_5=H$; $X=CH_2$; $R_3=$allyloxy; $R_4=Cl$ suprofen (INN) $R_1=R_2=R_4=R_5=H$; $X=CH(CH_3)$; $R_3=$2-thenoyl;

cliprofen (INN) $R_1=R_2=R_5=H$; $X=CH(CH_3)$; $R_3=$2-thenoyl; $R_4=Cl$;

fenbufen (INN) $R_1=R_2=R_4=R_5=H$; $X=COCH_2CH_2$; $R_3=$phenyl;

fenoprofen (INN) $R_1=R_2=R_3=R_5=H$; $X=CH(CH_3)$; $R_4=$phenoxy;

lexofenac (INN) $R_1=R_2=R_4=R_5=H$; $X=CH_2$; $R_3=$3-oxo-1-cyclohexenyl;

ximoprofen (INN) $R_1=R_2=R_4=R_5=H$; $X=CH(CH_3)$; $R_3=$3-oximino-cyclohexyl;

fenclofenac (INN) $R_1=R_2=R_3=R_4=H$; $X=CH_2$; $R_5=$2,4-dichlorophenoxy;

ketoprofen (INN) $R_1=R_2=R_3=R_5=H$; $X=CH(CH_3)$; $R_4=$benzoyl;

amfenac (INN) $R_1=R_2=R_3=H$; $X=CH_2$; $R_4=$benzoyl; $R_5=$amino;

fenclorac (INN) $R_1=R_2=R_5=H$; $X=CH(Cl)$; $R_3=$cyclohexyl; $R_4=Cl$;

naproxen (INN) $R_1+R_2=CH=CH=C(OCH_3)=CH—$; $X=CH(CH_3)$, $R_3=R_4=R_5=H$;

bucloxic acid (INN) $R_1=R_2=R_5=H$; $X=COCH_2CH_2$; $R_3=$cyclohexyl; $R_4=Cl$;

4-cyclopropylmethoxy-3-chlorophenyl acetic acid; $R_1=R_2=R_5=H$; $X=CH_2$; $R_3=$cyclopropylmethoxy; $R_4=Cl$;

3-(4-chlorobenzoyl)-2-aminophenyl acetic acid: $R_1=R_2=R_3=H$; $R_4=$4-chlorobenzoyl; $R_5=$amino; $X=CH_2$;

4-biphenylacetic acid: $R_1=R_2=R_4=R_5=H$; $X=CH_2$; $R_3=$phenyl;

4-cyclopropylcarbonyl-phenylacetic acid: $R_1=R_2=R_4=R_5=H$; $X=CH_2$; $R_3=$cyclopropylcarbonyl.

Other advantageous phthalidyl esters of arylalkanoic acids having analgesic and anti-inflammatory activity, which are within the scope of the present invention and which are not embraced by the general formula I, are the phthalidyl esters of the compounds hereinbelow indicated by their INN and/or by their chemical name:

3-hydroxy-4-(4-biphenylyl)-butyric acid described in the U.S. Pat. No. 3,462,483;

oxepinac (INN) 6,11-dihydro-11-oxodibenz[b,e]oxepin-3-acetic acid described in the French Pat. No. 2,245,356;

isoxepac (INN) 6,11-dihydro-11-oxodibenz[b,e]oxepin-2-acetic acid, described in the French Pat. No. 2,242,976;

carprofen (INN) 6-chloro-α-methylcarbazole-2-acetic acid, described in the U.S. Pat. No. 3,896,145;

benoxaprofen (INN) 2-(4-chlorophenyl)-α-methyl-5-benzoxazoleacetic acid, described in the French Pat. No. 2,184,966;

2-(3-phenyl-7-benzofuranyl)-propionic acid, described in U.S. Pat. No. 3,682,976;

metiazinic acid (INN) 10-methylphenotiazin-2-ylacetic acid;

protizinic acid (INN) 2-(7-methoxy-10-methyl-2-phenotiazinyl)-propionic acid, described in the U.S. Pat. No. 3,450,698;

furofenac (INN) 5-(2-ethyl-2,3-dihydro-benzofuranyl)acetic acid, described in the U.S. Pat. No. 4,029,811;

cicloprofen (INN) 2-(α-methyl)fluoreneacetic acid, described in the U.S. Pat. No. 3,859,340;

2(2-phenyl-5-benzothiazolyl)-propionic acid described in the U.S. Pat. No. 3,895,028;

2-(2-xanthone)propionic acid described in the U.S. Pat. No. 3,678,077;

pranoprofen (INN) 2-[5H-[1]benzopyrano[2,3b]pyridin-7-yl propionic acid described in the French Pat. No. 2,193,593.

It is another object of the present invention to provide a method for improving the pharmacological characteristics of arylalkanoic acids having analgesic and anti-inflammatory activity. The method of the present invention consists of introducing, through an ester bond, a phthalidyl group into the molecule of said arylalkanoic acids having analgesic and anti-inflammatory activity, in order to obtain the new phthalidyl esters of said arylalkanoic acid having analgesic and anti-inflammatory activity.

A particularly preferred method consists of introducing, through an ester bond, a phthalidyl group, into the molecule of an arylalkanoic acid having analgesic and anti-inflammatory activity or formula

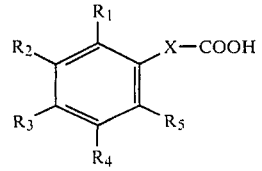

II in which $R_1$, $R_2$, $R_3$, $R_4$, $R_5$ and X have the above-stated meaning, in order to obtain a phthalidyl ester having the formula I above.

The new phthalidyl esters of the arylalkanoic acids having analgesic and anti-inflammatory activity of the present invention are prepared by reacting equimolecular amounts of the corresponding free acids or of the potassium, sodium or ammonium salts thereof with a 3-halophthalide in an organic solvent.

Suitable 3-halophthalides are the 3-chloro and, preferable the 3-bromophthalide.

As organic solvent, an halogenated solvent, such as methylene chloride, or a polar aprotic solvent, such as dimethylformamide, dimethylacetamide, dimethylsulfoxide and the like, is preferably employed.

The reaction time depends upon the temperature: at room temperature, i.e. between 20° and 24° C., the reaction time varies from 20 to 30 hours, preferably from 22 to 27 hours and more advantageously from 24 to 26 hours.

If a free acid is used as starting material, the reaction is carried out in the presence of a proton acceptor, i.e. an organic base such as triethylamine, 1-methylpiperidine and the like or an inorganic base such as sodium or potassium hydroxide, sodium or potassium carbonate, sodium or potassium bicarbonate and the like. Preferred starting materials are those embraced by the formula II above or their sodium, potassium or ammonium salts.

The new compounds of the present invention show interesting pharmacological properties. More particularly, they are at least as active as the corresponding free arylalkanoic acids having analgesic and anti-inflammatory activity, but, in general, they exhibit an enhanced analgesic and anti-inflammatory activity with respect to the corresponding arylalkanoic acids.

Table I below summarizes the acute toxity, expressed as $DL_{50}$ in rats and in mice, the analgesic activity, expressed as $DE_{50}$ in the tail compression test, and the anti-inflammatory activity, expressed as $DE_{50}$ in the carrageenin-induced paw edema test, for eight representative compounds of the present invention in comparison with that of the corresponding free acids.

The compounds under examination are the following:

Compound I: 2-(4-isobutylphenyl)propionic acid,

Compound IA: phthalidyl 2-(4-isobutylphenyl)propionate;

Compound II: d-2-(6-methoxy-2-naphthyl)propionic acid,

Compound IIA: phthalidyl d-2-(6-methoxy-2-naphthyl)propionate;

Compound III: 2-(3-benzoylphenyl)propionic acid,

Compound IIIA: phthalidyl 2-(3-benzoylphenyl)propionate;

Compound IV: 2-[4-(1-oxo-2-isoindolinyl)phenyl]propionic acid,

Compound IVA: phthalidyl 2-[4-(1-oxo-2-isoindolinyl)phenyl]propionate;

Compound V: 4-allyloxy-3-chlorophenylacetic acid,

Compound VA: phthalidyl 4-allyloxy-3-chlorophenylacetate;

Compound VI: 2-(2,6-dichloroanilino)phenylacetic acid,

Compound VIA: phtalidyl 2-(2,6-dichloroanilino)phenylacetate;

Compound VII: 4-(4-biphenylyl)-4-oxobutyric acid,

Compound VIIA: phthalidyl 4-(4-biphenylyl)-4-oxobutyrate;

Compound VIII: 4-biphenylylacetic acid;

Compound VIIIA: phtalidyl 4-biphenylylacetate.

The tail compression test has been carried out in mice according to the method described by C. Bianchi (Brit. J. Pharmacol., 11, 104; 1956) by determining the time in seconds between the algic stimulation and the reaction of the mouse.

For the determination of the anti-inflammatory activity, the carrageenin-induced rat paw edema test, as a modification of the method reported by C. A. Winth et al. (Proc. Soc. Exptl. Biol. Med., 111, 544; 1962) has been used. This method involves the reduction of the edema caused by the injection of a 2% carrageenin solution in the rat paw. The compounds under examination have been administered by oral route one hour before the injection of the edemigenic agent. The volume of the rat paw has been measured by a plethismometer before and 5 hours after the injection of the carrageenin.

TABLE I

| | $DL_{50}$* acute toxicity mg/kg | | Analgesic activity | Anti-inflammatory activity |
|---|---|---|---|---|
| | mouse | rat | $DE_{50}$ | $DE_{50}$ |
| Compound I | 877.16 | 1480.00 | 5.28* | 59.14* |
| Compound IA | 1536.34 | 2180.36 | 2.08 | 4.30 |
| Compound II | 1190.72 | 574.79 | 21.90* | 16.36 |
| Compound IIA | 2142.53 | 1058.90 | 5.81 | 14.82 |
| Compound III | 364.78 | 116.00 | 3.01* | 4.36 |
| Compound IIIA | 513.50 | 342.45 | 1.34 | 5.15 |
| Compound IV | 536.32 | 62.34 | 2.58 | 5.45 |
| Compound IVA | 987.43 | 233.89 | 2.18 | 4.45 |
| Compound V | 1094.66 | 1029.75 | 2.43 | 1058.45* |
| Compound VA | 2060.00 | 1767.00 | 2.50 | 117.34 |
| Compound VI | 3689.03 | 180.94 | 3.81 | 189.54* |
| Compound VIA | 592.60 | 342.00 | 4.33 | 144.21 |
| Compound VII | 839.34 | 660.40 | 4.02* | 30.53* |
| Compound VIIA | 1401.45 | 1375.34 | 2.95 | 20.08 |
| Compound VIII | 750.35 | 635.40 | 3.07 | 21.79* |
| Compound VIIIA | 1405.10 | 1170.23 | 2.78 | 13.28 |

*The data given are statistically significant

Furthermore, the phtalidyl esters of the arylaalkanoic acids having analgesic and anti-inflammatory activity, besides the enhanced pharmacological activity and the reduced acute toxicity with respect to the corresponding free acids, possess an ulcerogenic potential activity far less pronounced than that of the corresponding free acids.

The ulcerogenic activity of the above mentioned eight representative compounds of the present invention in comparison with that of the corresponding free acids is given in table II below. The ulcerogenic activity is expressed as $DU_{50}$ in rats according to the method described by Dabrodie et al (Science, 170, 183; 1970).

TABLE II

| Compound | $DU_{50}$* (mg/kg) |
|---|---|
| Compound I | 85.90 |
| Compound IA | 143.61 |
| Compound II | 78.70 |
| Compound IIA | 132.80 |

TABLE II-continued

| Compound | $DU_{50}$* (mg/kg) |
|---|---|
| Compound III | 31.50 |
| Compound IIIA | 76.72 |
| Compound IV | 51.10 |
| Compound IVA | 116.00 |
| Compound V | 213.88 |
| Compound VA | 380.00 |
| Compound VI | 13.10 |
| Compound VIA | 26.06 |
| Compound VII | 78.70 |
| Compound VIIA | 145.54 |
| Compound VIII | 65.30 |
| Compound VIIIA | 185.72 |

*The data given are statistically significant.

The toxic symptoms are, for both the phthalidyl esters and the corresponding free acids, of the neurodepressive type. From the autoptic examination, it appears that the animals treated with the free acids present interstitial ulcers and lesions with bleeding. On the other hand, the animals treated with the phthalidyl esters of the present invention present an hyperemic gastric mucosa only.

From the data given above, it can be seen that, besides an improved pharmacological activity, the compounds of the present invention show a better tolerability, with respect to the reference compounds, both as far as the acute toxicity ($DL_{50}$) and the ulcerogenic potential ($DU_{50}$) are concerned.

Thus, it is a further object of the present invention to provide pharmaceutical compositions containing, as active ingredients, the phthalidyl esters of the arylalkanoic acids having analgesic and anti-inflammatory activity in admixture with solid, liquid or semiliquid pharmaceutically acceptable carriers for parenteral, oral, topical or rectal administration.

Particularly preferred are the pharmaceutical compositions containing, as active ingredients, the phthalidyl esters of the arylalkanoic acids having analgesic and anti-inflammatory activity of formula I above, in admixture with a pharmaceutical carrier.

The pharmaceutical compositions for oral administration include tablets, pills, gastro-resistant tablets, powders for reconstitution into a liquid oral preparation, syrups, granulates, capsules and the like.

As pharmaceutically acceptable carriers, the common excipients are used such as talc, lactose and the like.

Such compositions for oral use can also be mixed with lubricating agents, such as magnesium stearate.

The liquid composition for oral administration include syrups, emulsions, suspensions and elixirs which can be mixed with sweetening and flavouring agents. As liquid carriers water, hydroalcoholic solutions and paraffin can be conveniently used.

For oral administration, capsules containing a solid or a semiliquid preparation, or even the active ingredient without any excipient can be employed.

For parenteral administration, the active ingredient is mixed with a liquid carrier such as distilled water, propylene glycol, polyethylene glycol, vegetable oils and the organic esters thereof, such as ethyl oleate and the like.

All those injectable formulations can be sterilized by filtering membranes or sterilizing agents of both chemical and physical nature.

For rectal administration, the active ingredient is included in suppositories or in absorbable capsules admixed with carriers such as cocoa butter, stearates and waxes.

The active ingredients are included in the pharmaceutical compositions of the present invention at a dose of from about 10 mg to about 1000 mg per dosage unit.

Preferred dosage unit forms contain from about 25 to about 750 mg of active ingredient.

The pharmaceutical compositions of the present invention are administered to mammals, including humans, in order to alleviate pain and to treat inflammatory conditions.

The active ingredients are administered in an effective amount generally corresponding, on the molecular basis, to the effective dosage of the parent free arylalkanoic acids having analgesic and anti-inflammatory activity. However, due to their enhanced activity and to their reduced side effects, the phthalidyl esters can be administered at a lower or, preferably, at a higher dosage. The higher dosages have the advantage of giving better therapeutical response without any appreciable side effects.

The following Examples illustrate the invention without limiting it.

EXAMPLE 1

To a solution of 6.2 g of 2-(4-isobutylphenyl)propionic acid in 30 ml of chloroform and 3.4 g of triethylamine, a solution of 6.2 g of 3-bromophthalide in 20 ml of chloroform is added. The solution thus obtained is stirred 24 hours at room temperature (about +22° C.), the organic phase is washed with an aqueous solution of sodium bicarbonate, then with water and finally it is dried on anhydrous sodium sulfate and evaporated to dryness. The residue, crystallized from petroleum ether, yields 8.1 g of phthalidyl 2-(4-isobutylphenyl)propionate; m.p. 62°–65° C. IR: 1795 and 1780 cm$^1$

| Analysis for $C_{22}H_{18}O_5$ | C % | H % |
| --- | --- | --- |
| Calculated | 74.54 | 6.66 |
| Found | 74.57 | 6.50 |

Figure 1B:
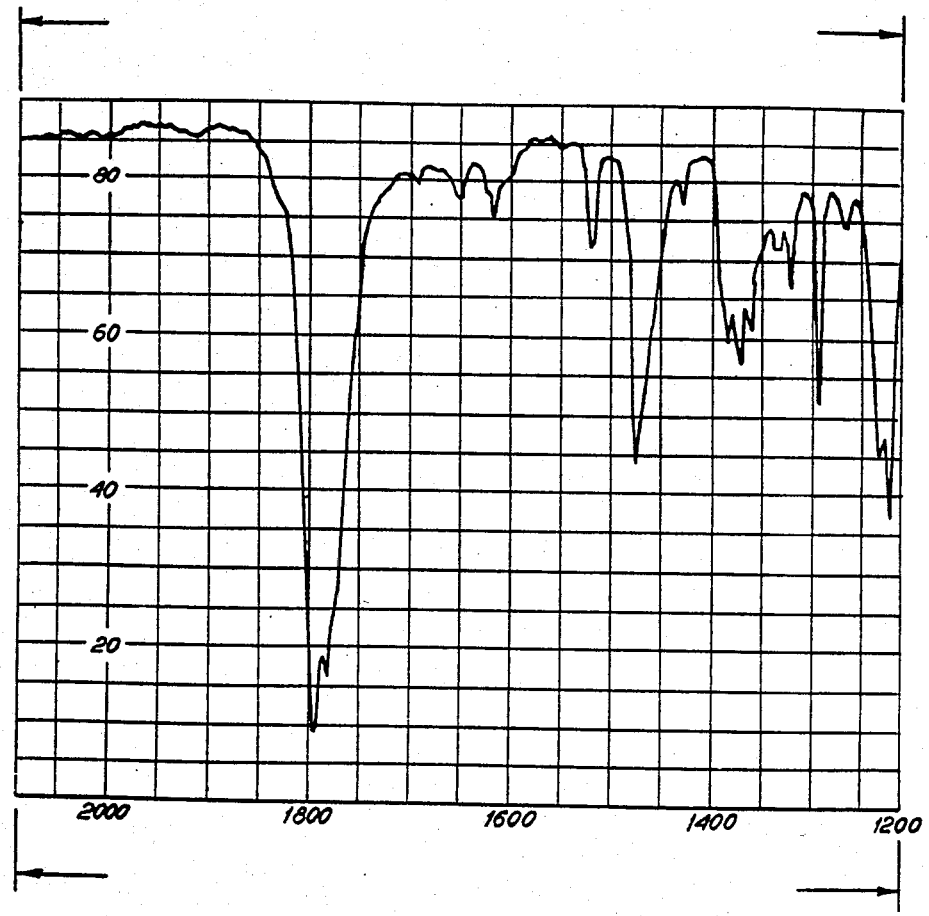
Figure 1C:
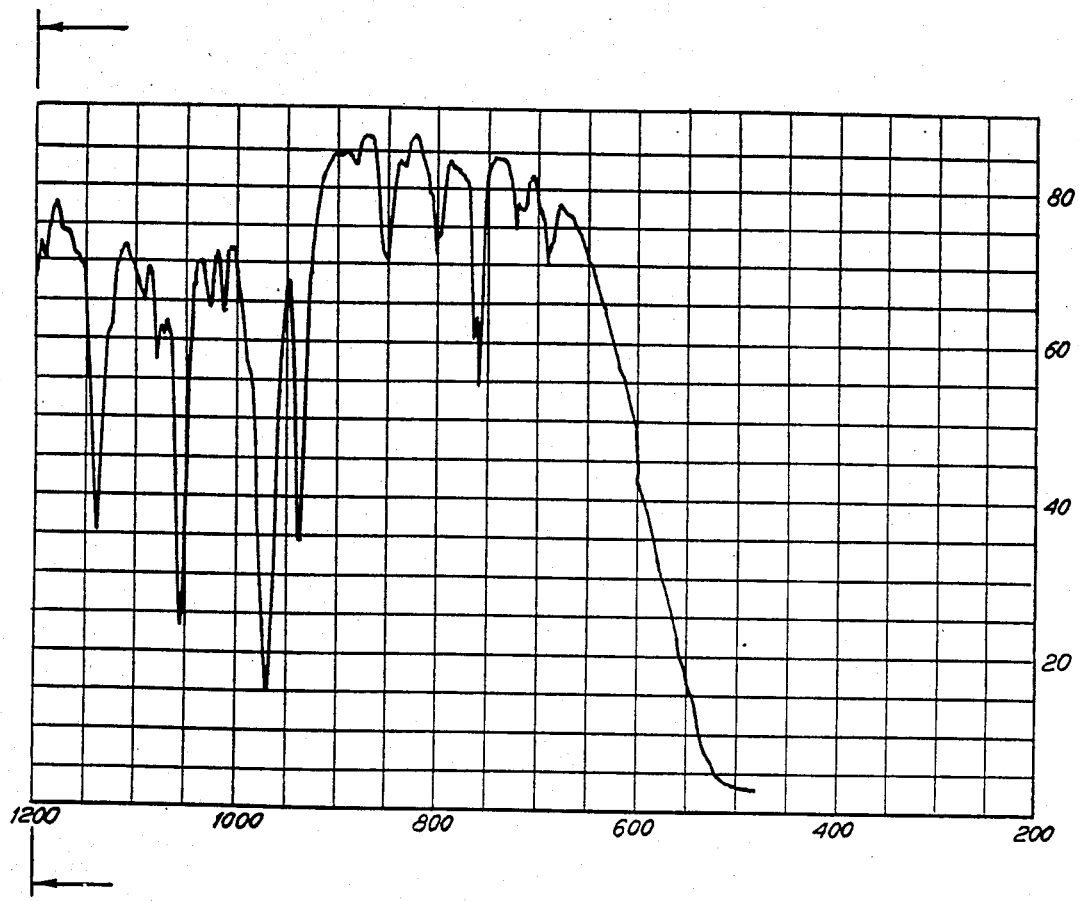
Figure 2:
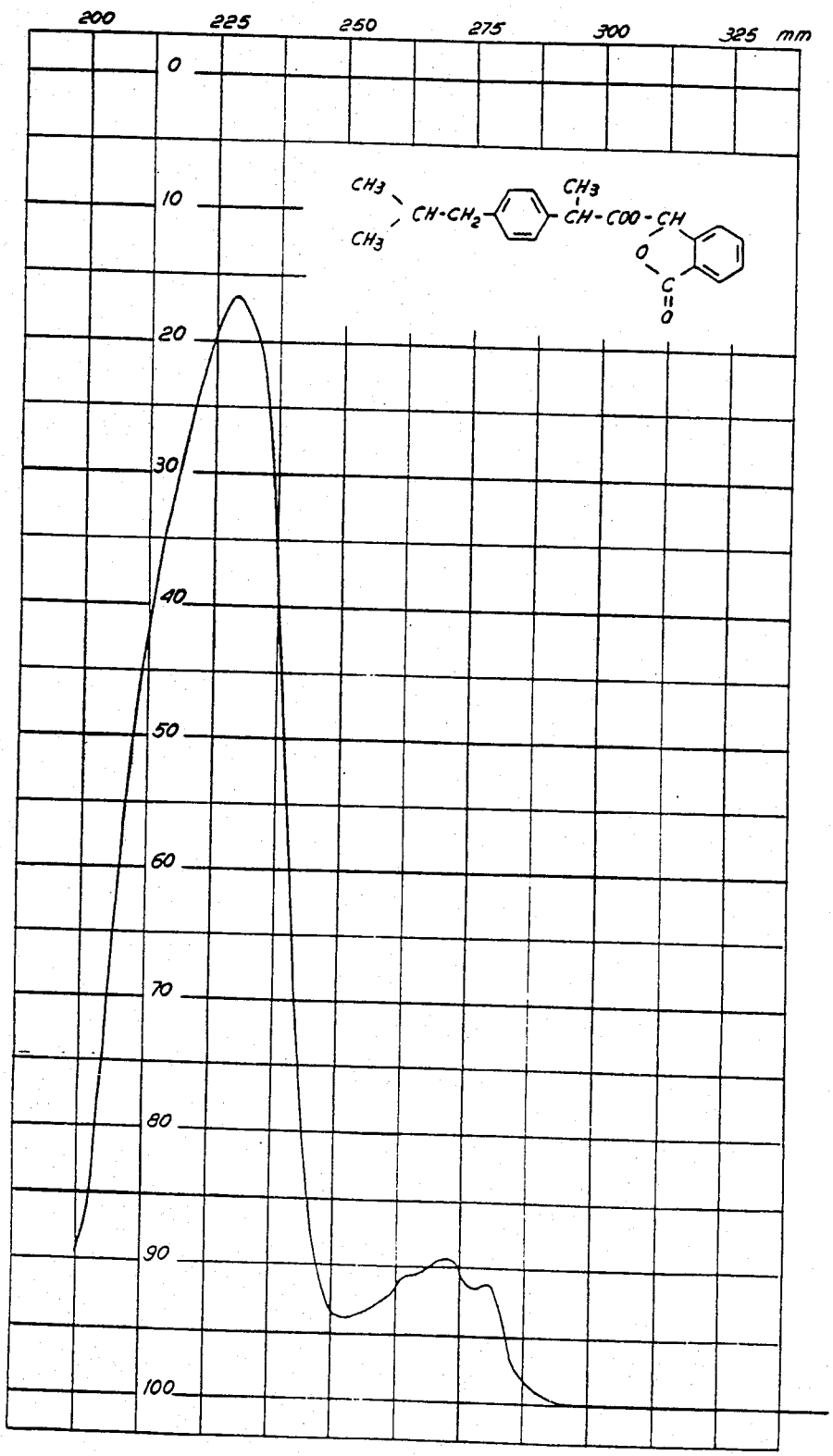
Figure 3A:
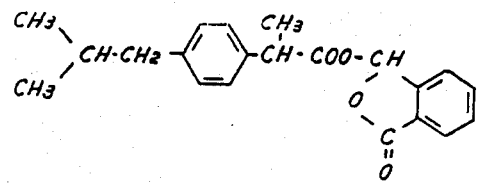
Figure 3A:
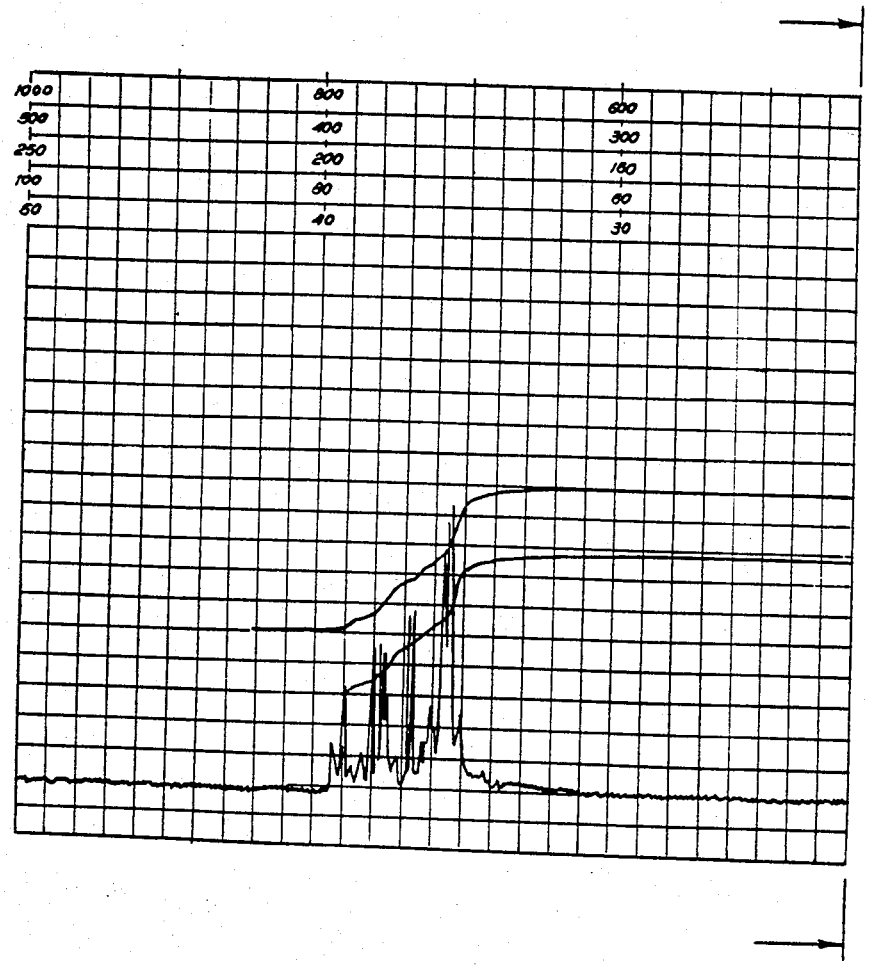
Figure 3B:
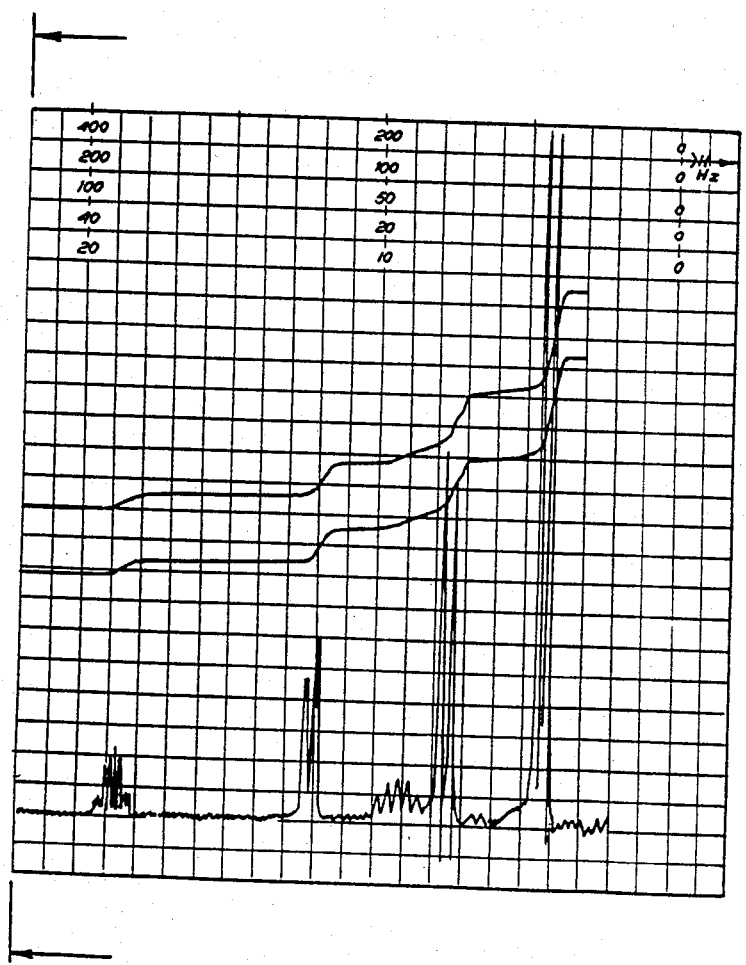

The IR spectrum of this compound is shown in FIGS. 1A, 1B and 1C, the UV spectrum in FIG. 2, and the NMR spectrum in FIGS. 3A and 3B. In the same manner, by reacting S-(2-fluoro-4-biphenylyl)propionic acid, 2-(4-cyclohexylphenyl)propionic acid, 2-[3-chloro-4-(2,5-dihydro-1H-pyrrolyl)phenyl]propionic acid, 2-[4-(1-cyclohexenyl)phenyl]propionic acid, 2-[4-(2-thenoyl)phenyl]propionic acid, 2-[3-chloro-4-(2-thenoyl)phenyl]propionic acid, 2-(3-phenoxyphenyl)propionic acid, 2-[4-(3-oximino-1-cyclohexyl)phenyl]propionic acid, 2-(6-chloro-2-carbazoyl)propionic acid, 2-(4-chlorophenyl-5-benzoazolyl)propionic acid, 2-(7-methoxy-10-methyl-2-phenotiazinyl)propionic acid, 2-(2-fluorenyl)propionic acid, 2-(2-phenyl-5-benzothiazolyl)propionic acid, 2-(10-oxo-2-xanthyl)propionic acid and 2-[5H-(1)-benzopyrano[2,3]pyridin-7-yl]propionic acid, respectively, with 3-bromophthalide,
phthalidyl 2-(2-fluoro-4-biphenylyl)proprionate,
phthalidyl 2-(4-cyclohexylphenyl)proprionate,
phthalidyl 2-[3-chloro-4-(2,5-dihydro-1H-pyrrolyl)phenyl]propionate,
phthalidyl 2-[4-(1-cyclohexenyl)phenyl]propionate,
phthalidyl 2-[4-(2-thenoyl)phenyl]propionate,
phthalidyl 2-[3-chloro-4-(2-thenoyl)phenyl]propionate,
phthalidyl 2-(3-phenoxyphenyl)propionate,
phthalidyl 2-[4-(3-oximino-1-cyclohexyl)phenyl]propionate,
phthalidyl 2-(6-chloro-2-carbazolyl)propionate,
phthalidyl 2-(4-chlorophenyl-5-benzoxazolyl)propionate,
phthalidyl 2-(7-methoxy-10-methyl-2-phenothiazinyl)propionate,
phthalidyl 2-(2-fluorenyl)propionate,
phthalidyl 2-(2-phenyl-5-benzothiazolyl)propionate,
phthalidyl 2-(10-oxo-2-xanthyl)propionate and,
phthalidyl 2-[5H-[1]benzopyrano[2,3b]pyridin-7-yl]propionate, respectively,
are obtained.

EXAMPLE 2

To a solution of 10.65 g of 3-bromophthalide in 100 ml of dimethylformamide, 11.5 g of sodium 2-(4-isobutylphenyl)propionate is added under stirring at room temperature. The reaction mixture is stirred 24 hours at room temperature, and it is then poured into 500 ml of ice water. After extraction with chloroform, the organic phase is washed with an aqueous solution of sodium bicarbonate, then with water and finally it is dried on anhydrous sodium sulfate and evaporated to dryness. The residue, crystallized from petroleum ether, yields 12.3 g of phthalidyl 2-(4-isobutylphenyl)propionate, having the same physico-chemical characteristics of the compounds of Example 1.

EXAMPLE 3

To a solution of 10.65 g of 3-bromophthalide in 100 ml of dimethylformamide is added 12.2 g of potassium 2-(4-isobutylphenyl)propionate under stirring at room temperature. The reaction mixture is stirred 24 hours at room temperature, and then poured into 500 ml of ice water. After extraction with chloroform, the organic phase is washed with an aqueous solution of sodium bicarbonate, then with water and finally dried on anhydrous sodium sulfate and evaporated to dryness. The residue, crystallized from petroleum ether, yields 11.8 g of phthalidyl 2-(4-isobutylphenyl)propionate having the same physico-chemical characteristics of the compound of Example 1.

EXAMPLE 4

To a stirred solution of 4.6 g of d-2-(6-methoxy-2-naphthyl)propionic acid in 20 ml of chloroform and 2.2 g of triethylamine at room temperature is added a solution of 4.3 g of 3-bromophthalide in 20 ml of chloroform. The solution thus obtained is stirred 24 hours at room temperature, the organic phase is washed with an aqueous solution of sodium bicarbonate, then with water and finally dried on anhydrous sodium sulfate and evaporated to dryness. The residue, crystallized from ethanol, yields 6.2 g of phthalidyl d-2-(6-methoxy)-2-naphthyl)propionate: m.p. 117°–119° C.

Figure 4A:
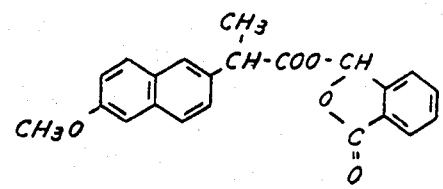
Figure 4A:
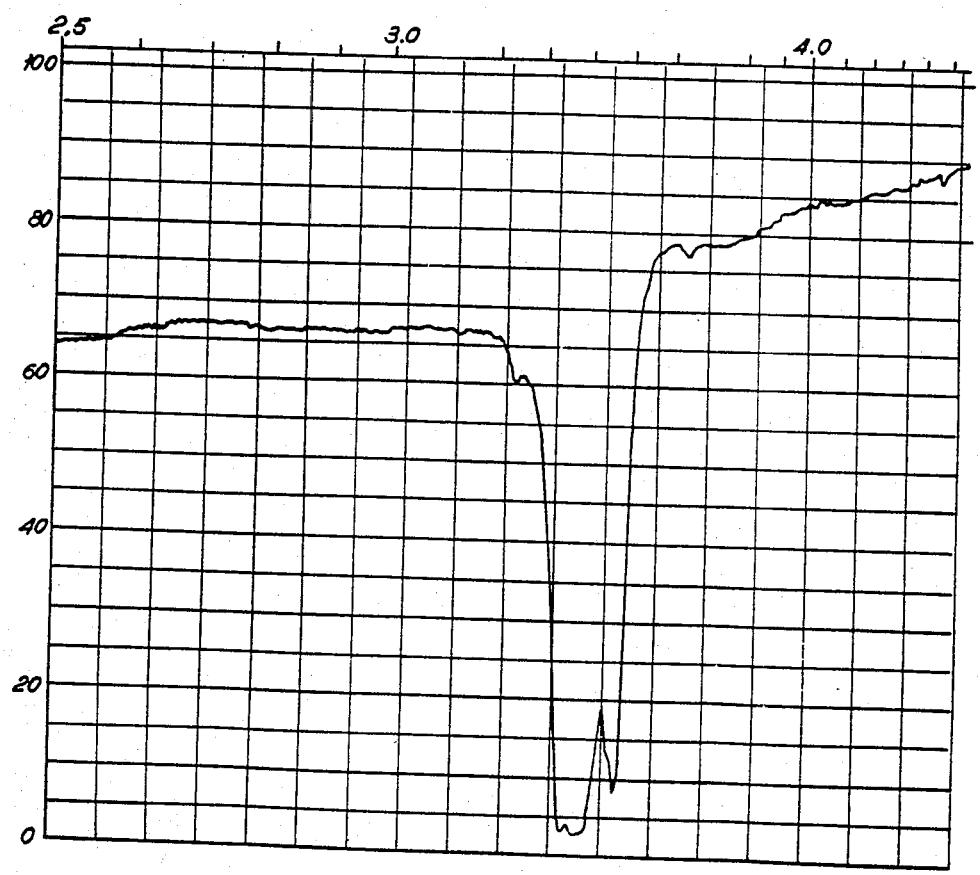
Figure 4B:
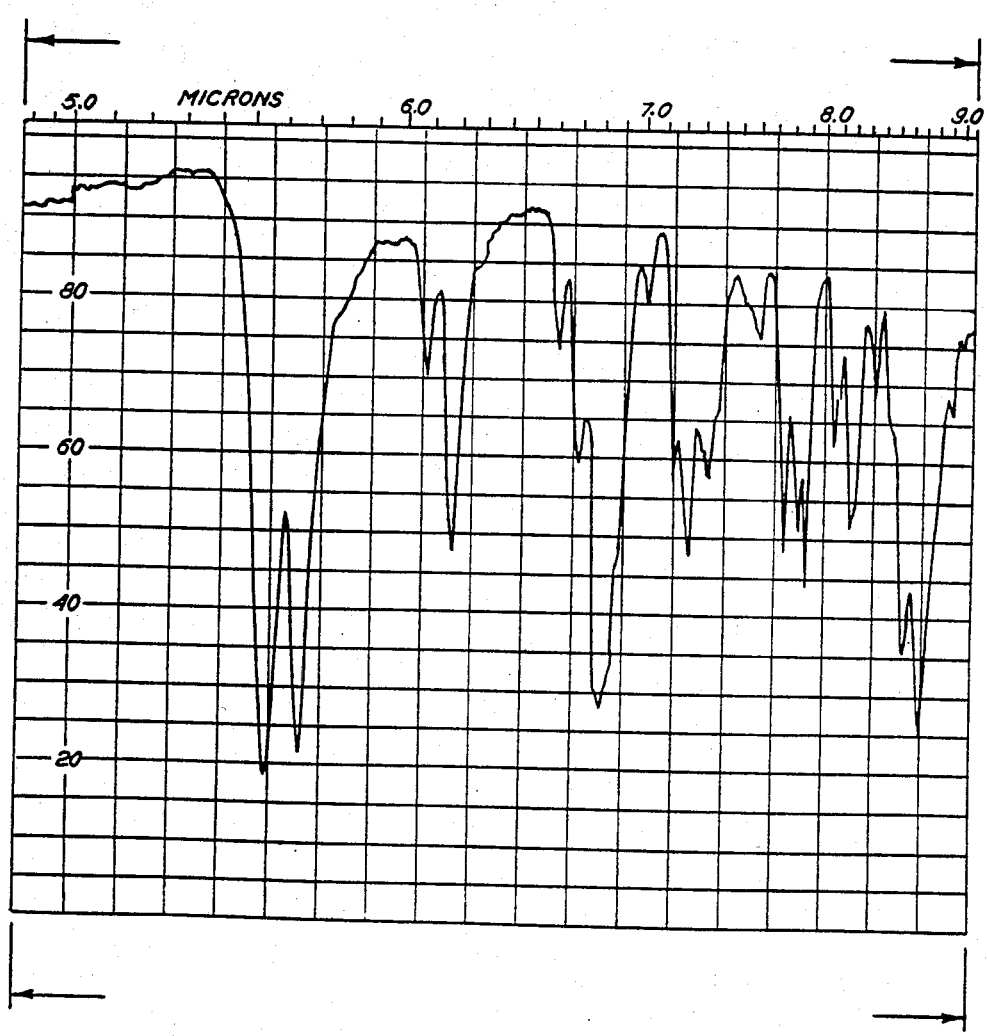
Figure 4C:
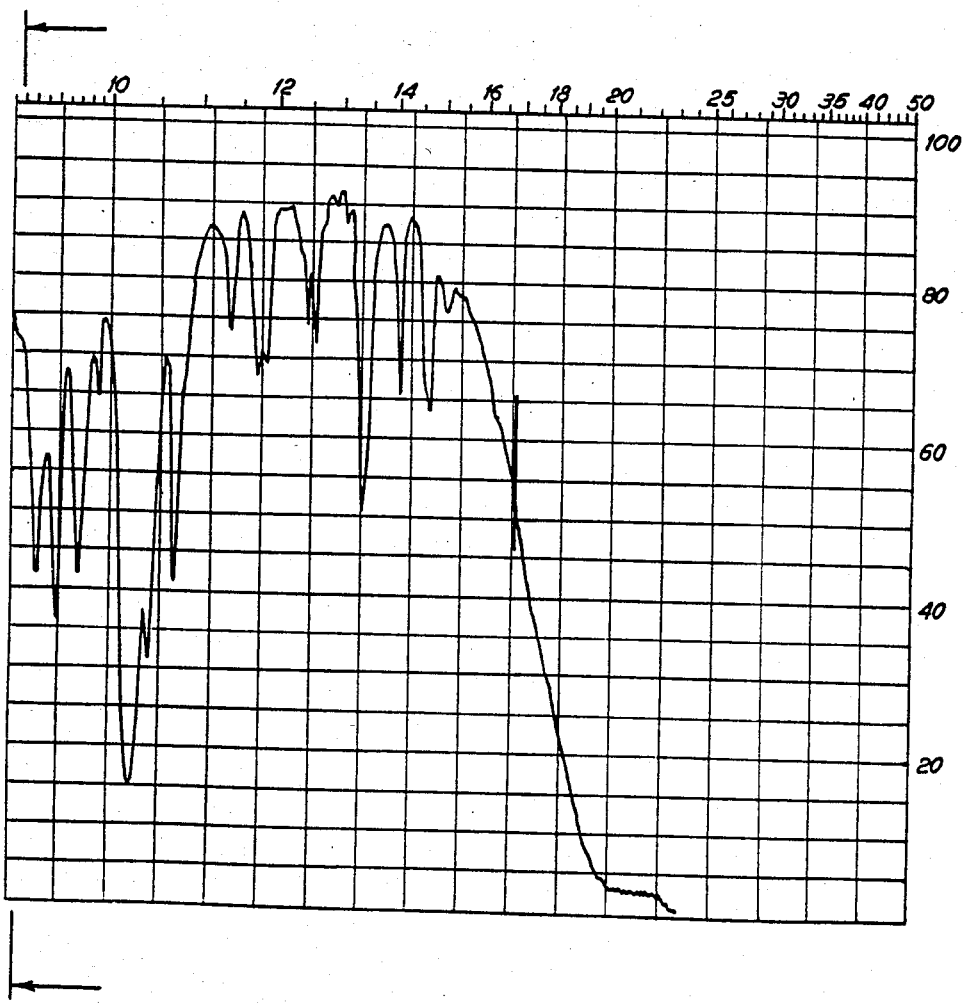
Figure 5:
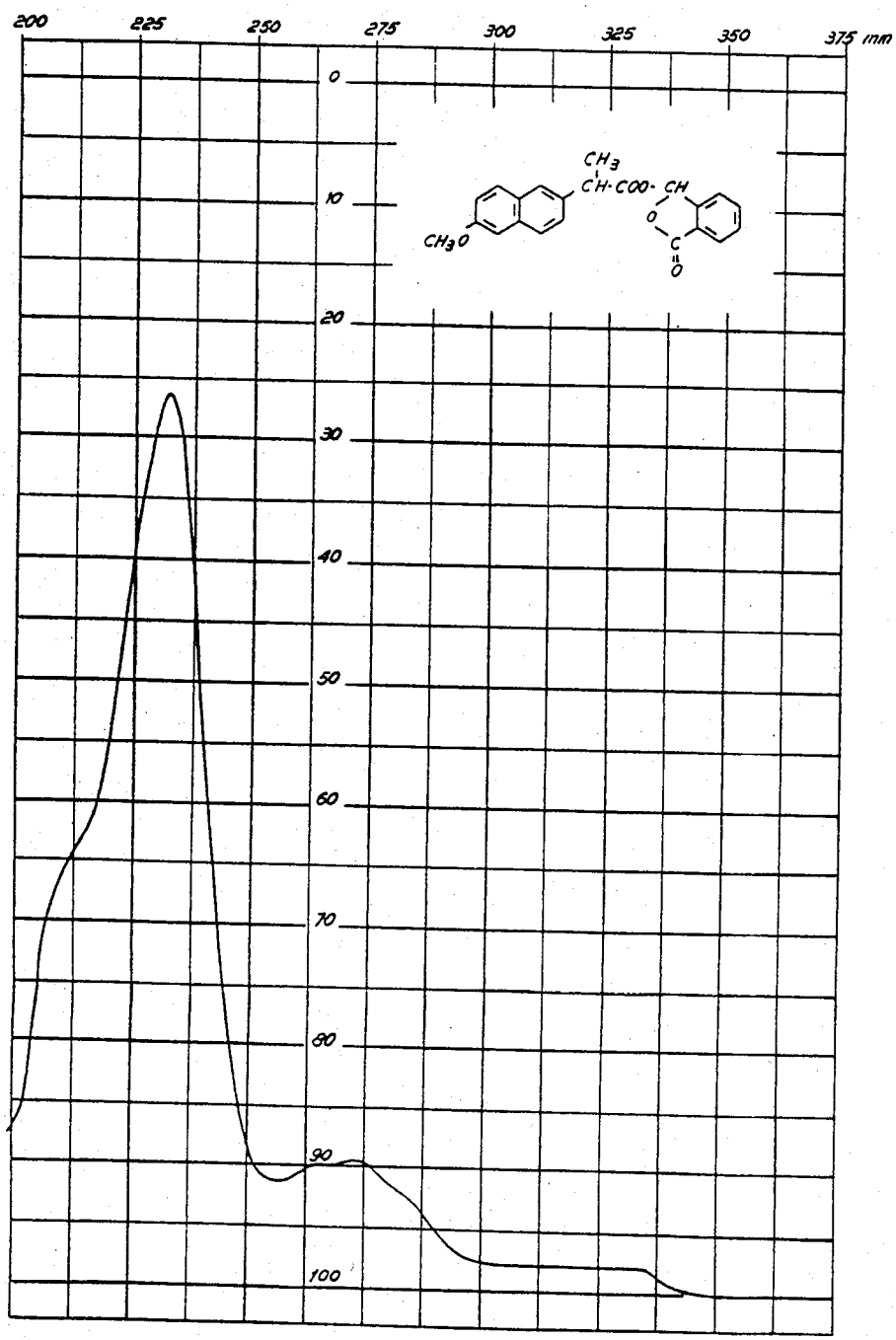
Figure 6A:
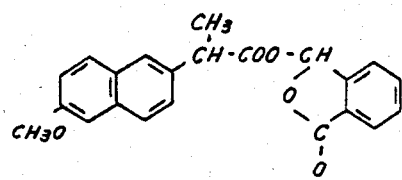
Figure 6A:
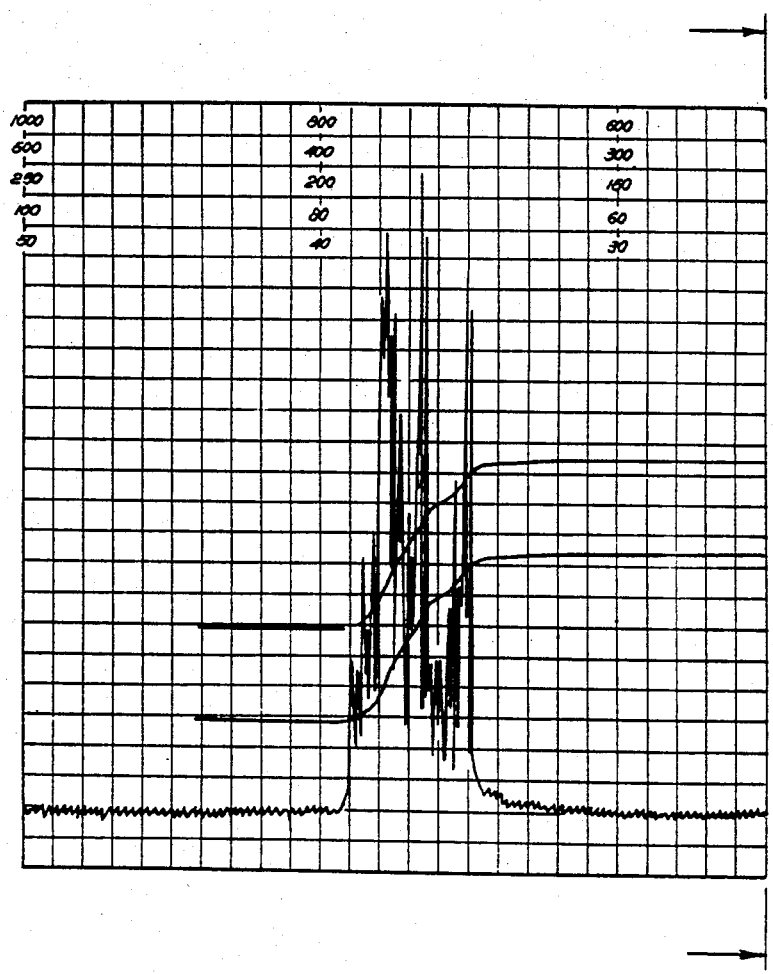
Figure 6B:
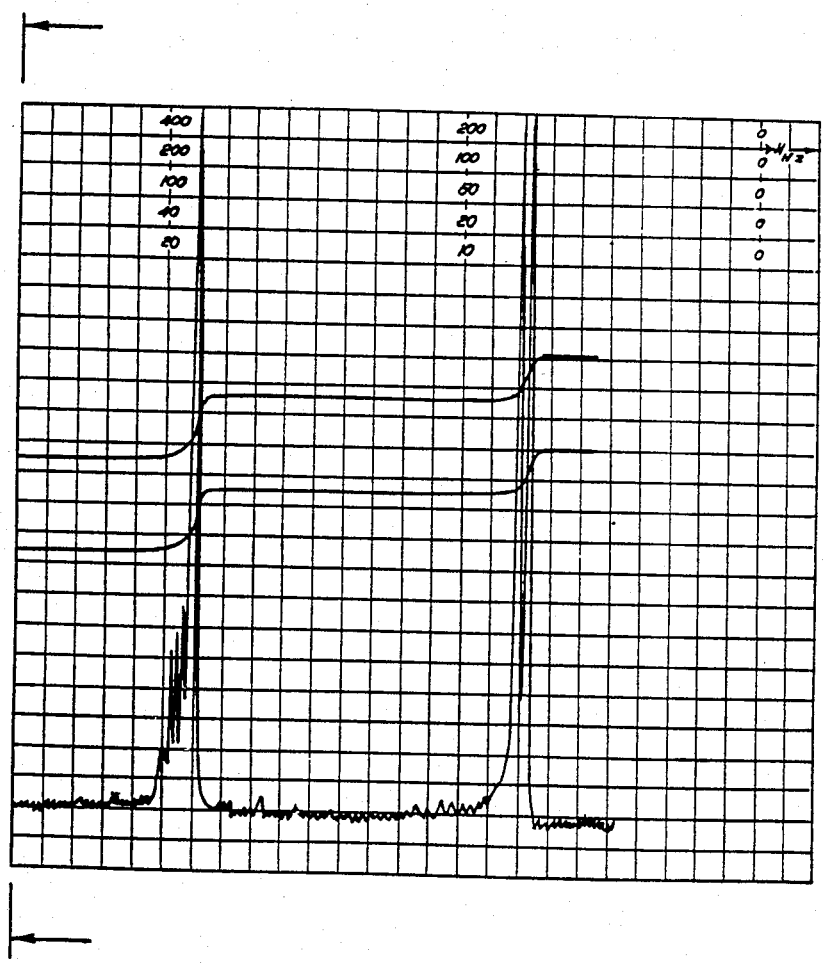

The IR spectrum is shown in FIGS. 4A, 4B and 4C, the UV spectrum in FIG. 5 and the NMR spectrum in FIGS. 6A and 6B.

| Analysis for $C_{22}H_{18}O_5$ | C % | H % |
| --- | --- | --- |
| Calculated | 72.92 | 5.01 |
| Found | 72.85 | 4.94 |

EXAMPLE 5

To a stirred solution, at room temperature, of 5.3 g of 3-bromophthalide in 50 ml of dimethylformamide is added 6.3 g of sodium d-2-(6-methoxy-2-naphthyl)propionate. The reaction mixture is stirred 24 hours at room temperature, and then poured into 250 ml of ice water. After extraction with chloroform, the organic phase is washed with an aqueous solution of sodium carbonate, then with water and finally it is dried on anhydrous sodium sulfate and evaporated to dryness. The residue, crystallized from ethanol, gives 6.7 g of phthalidyl d-2-(6-methoxy-2-naphthyl)propionate having the same physico-chemical characteristics of the compounds of Example 4.

EXAMPLE 6

To a stirred solution of 5.3 g of 3-bromophthalide in 50 ml of dimethylformamide is added, at room temperature, 6.7 g of potassium d-2-(6-methoxy-2-naphthyl)propionate. The reaction mixture is stirred 24 hours at room temperature, and then poured into 250 g of ice water. After extraction with chloroform, the organic phase is washed with an aqueous solution of sodium carbonate, then with water and finally it is dried on anhydrous sodium sulfate and evaporated to dryness. The residue, crystallized from ethanol, gives 6.3 g of phthalidyl d-2-(6-methoxy-2-naphthyl)propionate having the same physico-chemical characteristics of the compound of Example 4.

EXAMPLE 7

To a solution of 7.6 g of 2-(3-benzoylphenyl)propionic acid in 30 ml of chloroform and 3.4 g of triethylamine is added a solution of 6.2 g of 3-bromophthalide in 20 ml of chloroform. The solution thus obtained is stirred 25 hours at room temperature, the organic phase is washed with an aqueous solution of sodium bicarbonate, then with water and finally dried on anhydrous sodium sulfate and evaporated to dryness to give the phthalidyl 2-(3-benzoylphenyl)propionate; yield 79%.

| Analysis for $C_{24}H_{18}O_5$ | C % | H % |
| --- | --- | --- |
| Calculated | 74.60 | 4.69 |
| Found | 74.57 | 4.63 |

EXAMPLE 8

To a solution of 8.4 g of 2-[4-(1-oxo-2-isoindolinyl)-phenyl]propionic acid in 40 ml of chloroform and 3.4 of triethylamine is added a solution of 6.2 g of 3-bromophthalide in 20 ml of chloroform. The solution thus obtained is stirred 24 hours at room temperature, the organic phase is washed with an aqueous solution of sodium bicarbonate, then with water and finally it is dried on anhydrous sodium sulfate and evaporated to dryness to yield the phthalidyl 2-[4-(1-oxo-2-isoindolinyl)-phenyl]propionate; yield 75%.

| Analysis for $C_{25}H_{19}O_5$ | C % | H % | N % |
| --- | --- | --- | --- |
| Calculated | 72.63 | 4.63 | 3.39 |
| Found | 72.66 | 4.69 | 3.36 |

EXAMPLE 9

To a solution of 6.6 g of 4-allyloxy-9-chlorophenylacetic acid in 30 ml of chloroform and 3.4 g of triethylamine is added a solution of 6.2 g of 3-bromophthalide in 20 ml of chloroform. The solution thus obtained is stirred 24 hours at room temperature, the organic phase is washed with an aqueous solution of sodium bicarbonate, then with water and finally it is dried on anhydrous sodium sulfate and evaporated to dryness to give the phthalidyl 4-allyloxy-3-chlorophenylacetic acid; yield 78%.

| Analysis for $C_{19}H_{15}O_5$ | C % | H % |
| --- | --- | --- |
| Calculated | 63.61 | 4.21 |
| Found | 63.40 | 4.19 |

In the same manner, by reacting 4-isobutylphenylacetic acid, 4-(3-oxo-1-cyclohexenyl)-phenylacetic acid, 2-(2,4-dichlorophenoxy)-phenylacetic acid, 2-amino-3-benzoyl-phenylacetic acid, 3-chloro-4-cyclopropylmethoxy-phenylacetic acid, 2-amino-3-(4-chlorobenzoyl)-phenylacetic acid, 4-cyclopropylcarbonylphenylacetic acid, 6,11-dihydro-11-oxobenz[b,e]oxepin-3-acetic acid, 6,11-dihydro-11-oxodibenz[b,e]oxepin-2-acetic acid and 5-(2-ethyl-2,3-dihydrobenzofuranyl)-acetic acid, respectively, with 3-bromophthalide, phthaldiyl 4-isobutylphenylacetate;
phthalidyl 4-(3-oxo-1-cyclohexenyl)-phenylacetate;
phthalidyl 2-(2,4-dichlorophenoxy)-phenylacetate;
phthalidyl 2-amino-3-benzoyl-phenylacetate;
phthalidyl 3-chloro-4-cyclopropylmethoxy-phenylacetate;
phthalidyl 2-amino-3-(4-chlorobenzoyl)-phenylacetate;
phthalidyl 4-cyclopropylcarbonyl-phenylacetate;
phthalidyl 6,11-dihydro-11-oxodibenz[b,e]oxepin-3-acetate;
phthalidyl 6,11-dihydro-11-oxodibenz[b,e]oxepin-2-acetate;
and
phthalidyl 5-(2-ethyl-2,3-dihydrobenzofuranyl)acetate, respectively,
are obtained.

EXAMPLE 10

To a stirred solution of 10.65 g of 3-bromophthalide in 120 ml of dimethylformamide at room temperature is added 15.9 g of sodium 2-(2,6-dichloroanilino)-phenylacetate. The reaction mixture is stirred 24 hours at the room temperature, and then poured into 500 ml of ice water. After extraction with chloroform, the aqueous phase is washed with an aqueous solution of sodium bicarbonate, then with water and finally it is dried on anhydrous sodium sulfate and evaporated to dryness to yield the phthalidyl 2-(2,6-dichloroanilino)-phenylacetate; yield 70%.

| Analysis for $C_{22}H_{15}Cl_2NO_4$ | C % | H % | N % |
| --- | --- | --- | --- |
| Calculated | 61.70 | 3.53 | 3.27 |
| Found | 61.67 | 3.50 | 3.25 |

EXAMPLE 11

To a solution of 7.5 g of 4-(4-biphenylyl)-4-oxobutyric acid in 40 ml of chloroform and 3.4 g of triethylamine is added a solution of 6.2 g of 3-bromophthalide in 20 ml of chloroform. The solution thus obtained is stirred 24 hours at room temperature, the organic phase is washed with an aqueous solution of sodium bicarbonate, then with water and finally it is dried on anhydrous sodium sulfate and evaporated to dryness to give the phthalidyl 4-(4-biphenylyl)-4-oxobutyrate; yield 73%.

| Analysis for $C_{24}H_{18}O_5$ | C % | H % |
|---|---|---|
| Calculated | 74.60 | 4.69 |
| Found | 74.56 | 4.65 |

In the same manner, by reacting 4-[(4-cyclohexyl-3-chloro)phenyl]-4-oxobutyric acid with 3-bromophthalide, phthalidyl 4-[(4-cyclohexyl-3-chloro)phenyl]-4-oxobutyrate is obtained.

EXAMPLE 12

To a solution of 6.3 g of 4-biphenylylacetic acid in 30 ml of chloroform and 3.4 g of triethylamine is added a solution of 6.2 g of 3-bromophthalide in 20 ml of chloroform. The solution thus obtained is stirred 24 hours at room temperature, the organic phase is washed with an aqueous solution of sodium bicarbonate, then with water and finally it is dried on anhydrous sodium sulfate and evaporated to dryness. The residue, crystallized from petroleum ether, gives the phthalidyl 4-biphenylylacetate.

| Analysis for $C_{14}H_{12}O_2$ | C % | H % |
|---|---|---|
| Calculated | 79.24 | 5.66 |
| Found | 79.22 | 5.66 |

EXAMPLE 13

To a solution of 8.6 g of α-chloro-(3-chloro-4-cyclohexyl)phenylacetic acid in 40 ml of chloroform and 3.4 g of triethylamine is added a solution of 6.2 g of 3-bromophthalide in 20 ml of chloroform. The solution thus obtained is stirred 24 hours at room temperature, the organic phase is washed with an aqueous solution of sodium bicarbonate, then with water and finally it is dried on anhydrous sodium sulfate and evaporated to dryness to give the phthalidyl α-chloro-(3-chloro-4-cyclohexyl-phenylacetate; yield 70%.

| Analysis for $C_{14}H_{16}Cl_2O_2$ | C % | H % | Cl % |
|---|---|---|---|
| Calculated | 58.53 | 5.57 | 24.77 |
| Found | 58.51 | 5.56 | 24.71 |

EXAMPLE 14

To a solution of 7.7 g of 3-hydroxy-4-(4-biphenylyl)-butyric acid in 40 ml of chloroform and 3.4 g of triethylamine is added a solution of 6.2 g of 3-bromophtalide in 20 ml of chloroform. The solution thus obtained is stirred for 24 hours at room temperature, the organic phase is washed with an aqueous solution of sodium bicarbonate, then with water and finally it is dried on anhydrous sodium sulfate and evaporated to yield the phthalidyl 3-hydroxy-4-(4-biphenylyl)butyrate; yield 71%.

| Analysis for $C_{16}H_{16}O_3$ | C % | H % |
|---|---|---|
| Calculated | 75.00 | 6.25 |
| Found | 74.96 | 6.24 |

EXAMPLE 15

| Tablets | |
|---|---|
| Phthalidyl 2-(4-isobutylphenyl)propionate | 300 mg |
| Magnesium stearate | 50 mg |
| Lactose | 400 mg |

The active ingredient is granulated with a four percent w./v. aqueous solution of methyl cellulose. To the dried granules is added a mixture of the remainder of the ingredients and the final mixture is compressed into tablets. Satisfactory clinical response is obtained in adults suffering from pain or from inflammatory conditions with one tablet which can be repeated in 8 hours, if necessary. By repeated administration, the above composition shows less side effects, such as gastric pain, than an analogous composition containing 200 mg of the corresponding free acid.

EXAMPLE 16

| Suppositories. | |
|---|---|
| Phthalidyl 2-(4-isobutylphenyl)propionate | 600 mg |
| Fatty excipients | 700 mg |

The pulverized active substance is stirred into the melted suppository mass which has been cooled to 40° C. with the aid of an immersion homogenizer. The mass is then poured into molds which have previously been slightly cooled.

EXAMPLE 17

| Coated gastro-protected tablets. | |
|---|---|
| Phthalidyl d-2-(6-methoxy-2-naphthyl)propionate | 250 mg |
| Lactose | 250 mg |
| Talc | 50 mg |
| Gastro-resisting complex | 250 mg |

EXAMPLE 18

| Suppositories | |
|---|---|
| Phthalidyl 2-(3-benzoylphenyl)propionate | 75 mg |
| Water-dispersible fatty excipients | 290 mg |

EXAMPLE 19

| Tablets | |
|---|---|
| Phthalidyl 2-[4-(1-oxo-2-isoindolynil)phenyl]propionate | 200 mg |
| Lactose | 200 mg |
| Magnesium stearate | 20 mg |

EXAMPLE 20

| Ampoules | |
|---|---|
| Phthalidyl 4-allyloxy-3-chlorophenylacetate | 150 mg |
| Water-alcoholic solution q.s. to | 5 ml |

EXAMPLE 21

| Tablets | |
|---|---|
| Phthalidyl 4-(4-biphenylyl)-4-oxobutyrate | 300 mg |
| Talc | 50 mg |
| Magnesium stearate | 50 mg |
| Lactose | 200 mg |

Similarly, tablets containing 600 mg of phthalidyl 4-(4-biphenylyl)-4-oxobutyrate are prepared.

EXAMPLE 22

| Tablets | |
|---|---|
| Phthalidyl 2-(2,6-dichloroanilino)phenylacetate | 100 mg |
| Aerosil (registered TradeMark | 80 mg |
| Lactose | 220 mg |
| Potato starch | 90 mg |
| Tartaric acid | 5 mg |
| Magnesium stearate | 5 mg |

The active substance is mixed with Aerosil, lactose and half the given quantity of potato starch and is granulated with a 3.5% aqueous solution of the tartaric acid through a 1.5 mm mesh sieve. The moist substance is dried at 45° C. and again passed through the above sieve. The granulate is mixed with the remaining potato starch and the magnesium stearate and the mixture is compressed into tablets each weighing 500 mg.

EXAMPLE 23

| Tablets | |
|---|---|
| Phthalidyl 2-(2,6-dichloroanilino)phenylacetate | 75 mg |
| Lactose | 100 mg |
| Corn starch | 65 mg |
| Colloidal silicic acid | 2 mg |
| Soluble starch | 5 mg |
| Magnesium stearate | 3 mg |

The active ingredient is mixed with part of the excipients and granulated with a solution of soluble starch in water. After the granulate has been dried, the remaining excipients are added and the mixture is pressed into tablets each weighing 250 mg.

EXAMPLE 24

| Coated tablets | |
|---|---|
| Phthalidyl 2-(2,6-dichloroanilino)phenylacetate | 75 mg |
| Aerosil | 10 mg |
| Lactose | 60 mg |
| Potato starch | 13 mg |
| Tartaric acid | 1 mg |
| Magnesium stearate | 1 mg |

The active substance is mixed with Aerosil, lactose and half the given quantity of potato starch, and granulated with a 3.5% aqueous solution of the tartaric acid through a 1.5 mm mesh sieve. The moist substance is dried at 45° C. and again passed through the above sieve. The granulate is mixed with the remaining potato starch and the magnesium stearate and the mixture is compressed to form the coated tablet cores.

The coated tablet cores thus prepared are, by a known method, provided with a coating consisting essentially of sugar and talc. The finished coated tablets are polished with beeswax. Weight of the coated tablets is 240 mg.

EXAMPLE 25

| Capsules | |
|---|---|
| Phthalidyl 4-biphenylyl acetate | 200 mg |
| Powdered lactose | 100 mg |

The ingredients are mixed so as to evenly distribute the active ingredients through the lactose. The power is then packed into No. 1 empty gelatin capsule. Similarly, capsules containing 300 mg of phthalidyl 4-biphenylacetate are prepared.

EXAMPLE 26

| Capsules | |
|---|---|
| Phthalidyl α-chloro-(3-chloro-4-cyclohexyl)phenylacetate | 200 mg |
| Powdered lactose | 100 mg |

The preparation is similar to that of the Example 25.

EXAMPLE 27

| Capsules | |
|---|---|
| Phthalidyl 3-hydroxy-4-(4-biphenylyl)butyrate | 200 mg |
| Powdered lactose | 100 mg |

The preparation is the same as that of Example 25.

EXAMPLE 28

Capsules

By operating as described in Example 25, capsules containing 100 mg of phthalidyl 2-(2-fluoro-4-biphenylyl)propionate, 350 mg of phthalidyl 2-(2,4-dichlorophenoxy)phenylacetate, 500 mg of phthalidyl 2-(3-phenoxy)phenylpropionate and 400 mg of phthalidyl 4-[(4-cyclohexyl-3-chloro)phenyl]-4-oxobutyrate are prepared.

EXAMPLE 29

By operating as described in Examples 15 to 25, pharmaceutical compositions containing a therapeutically effective amount of any of the active ingredients described in Examples 1 to 14 are prepared.

EXAMPLE 30

Capsules 20,000 two-piece hard gelatin capsules for oral use, each containing 350 mg of phthalidyl 2-(4-isobutylphenyl)propionate are prepared from the following ingredients:

| | |
|---|---|
| Phthalidyl 2-(4-isobutylphenyl)propionate | 7,000 g |
| Lactose | 1,000 g |
| Starch | 300 g |
| Talc | 65 g |
| Magnesium stearate | 25 g |

The micronized phthalidyl 2-(4-isobutylphenyl)propionate is mixed with the starch-lactose mixture followed by talc and magnesium stearate. The final mixture is then encapsulated in the usual manner.

The capsules according to this invention, are used to alleviate pain and to treat inflammatory conditions. If necessary, a prolonged treatment of one capsule every 8 hours can be performed.

Similarly, capsules containing 200 mg of phthalidyl d-2-(6-methoxy-2-naphthyl)propionate and 100 mg of phthalidyl 2-(2,6-dichloroanilino)phenylacetate are also prepared by substituting 4,000 g of phthalidyl d-2-(6-methoxy-2-naphthyl)propionate and 2,000 g of phthalidyl 2-(2,6-dichloroanilino)phenylacetate for 7,000 g of phthalidyl 2-(4-isobutylphenyl)propionate in the above formulation.

EXAMPLE 31

Soft elastic capsules

One-piece soft elastic capsules for oral use, each containing 75 mg of phthalidyl 2-(2,6-dichloroanilino)phenylacetate are prepared in the usual manner by first dispersing the powdered active material in sufficient corn oil to render the material capsulatable.

Similarly, soft elastic capsules, containing a therapeutically effective amount of any of the active ingredients described in Examples 1 to 9 and 11 to 14, are prepared.

EXAMPLE 32

Aqueous preparation

An aqueous preparation for oral use containing in each 5 ml, 50 mg of phthalidyl 2-(2,6-dichloroanilino)phenylacetate is prepared from the following ingredients:

| | |
|---|---|
| Phthalidyl 2-(2,6-dichloroanilino)phenylacetate | 100 g |
| Methylparaben | 7.5 g |
| Propylparaben | 2.5 g |
| Saccharin sodium | 12.5 g |
| Glycerin | 3,000 ml |
| Tragacanth powder | 10 g |
| Orange oil flavour | 10 g |
| Deionized water q.s. to | 10,000 ml |

EXAMPLE 33

Parenteral suspension

A sterile aqueous suspension suitable for intramuscular route and containing, in each milliliter, 225 mg of phthalidyl 2-(4-isobutylphenyl)propionate is prepared from the following ingredients:

| | |
|---|---|
| Phthalidyl 2-(4-isobutylphenyl)propionate | 2.5 g |
| Polyethyleneglycol | 3 g |
| Sodium chloride | 0.9 g |
| Polysorbate 80 | 0.4 g |
| Sodium metabisulfite | 0.1 g |
| Methylparaben | 0.18 g |
| Propylparaben | 0.02 g |
| Water for injection q.s. to | 100 ml |

I claim:

1. Phthalidyl ester of arylakanoic acid having analgesic and anti-inflammatory activity having the formula

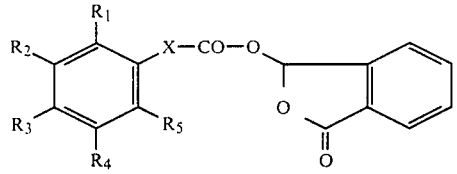

wherein $R_1$ is hydrogen; $R_3$ is hydrogen, alkyl having 1 to 5 carbon atoms, cyclopentyl, cyclohexyl, 3-oxocyclohexyl and its oxime, 1-cyclohexenyl, 3-oxo-1-cyclohexenyl, lower alkoxy having from 1 to 5 carbon atoms, lower alkenyloxy having 3 or 4 carbon atoms, cyclopropylmethoxy, cyclopropylcarbonyl, phenyl, or fluorophenyl; $R_4$ is hydrogen, fluorine, chlorine, phenoxy, benzoyl, or chlorobenzoyl; $R_5$ is hydrogen, amino, 2,4-dichlorophenoxy or 2,6-dichloroanilino; $R_2$ is hydrogen or together with $R_3$ is a —CH=CH—C(OCH$_3$)=CH— grouping and X is a CH$_2$, CH(CH$_3$), CH(Cl) or CO—CH$_2$—CH$_2$ group; provided that
   one or two of $R_2$, $R_3$, $R_4$ and $R_5$ is other than hydrogen; and
   when $R_2$ is joined to $R_3$ to form a —CH=CH—C(OCH$_3$)=CH— grouping, X is a —CH(CH$_3$); and
   when $R_3$ is other than hydrogen, $R_2$ and $R_5$ are hydrogen and $R_4$ is hydrogen, fluorine, chlorine; and
   when $R_4$ is phenoxy, benzoyl or chlorobenzoyl, $R_2$ and $R_3$ are hydrogen and $R_5$ is hydrogen or amino; and
   when $R_5$ is 2,6-dichloroanilino or 2,4-dichlorophenoxy, $R_2$, $R_3$ and $R_4$ are hydrogen.

2. Phthalidyl 2-(4-isobutylphenyl)propionate.
3. Phthalidyl d-2-(6-methoxy-2-naphthyl)propionate.
4. Phthalidyl 2-(3-benzoylphenyl)propionate.
5. Phthalidyl 4-allyloxy-3-chlorophenylacetate.
6. Phthalidyl 2-(2,6-dichloroanilino)phenylacetate.
7. Phthalidyl 4-(4-biphenylyl)-4-oxobutyrate.
8. Phthalidyl 4-biphenylylacetate.
9. An analgesic and antiinflammatory pharmaceutical composition containing, as active ingredient, an analgesic and antiinflammatory effective amount of a compound as claimed in one of claims 1 to 4 and 5 to 8 in admixture with a pharmaceutical carrier.
10. A pharmaceutical composition as claimed in claim 9 containing from about 10 to about 1000 mg of active ingredient per dosage unit.
11. A pharmaceutical composition as claimed in claim 10 containing from about 25 to about 750 mg of active ingredient.
12. A pharmaceutical composition with analgesic and anti-inflammatory activity in dosage unit form containing from about 25 to about 750 mg of an active ingredient selected from the group consisting of phthalidyl 2-(4-isobutylphenyl)propionate, phthalidyl d-2-(6-methoxy-2-naphthyl)propionate, phthalidyl 2-(3-benzoylphenyl)propionate, phthalidyl 4-allyloxy-3-chlorophenylacetate, phthalidyl 2-(2,6-dichloroanilino)phenylacetate, phthalidyl 4-(4-biphenylyl)-4-oxobutyrate and phthalidyl 4-biphenylylacetate in admixture with a pharmaceutical carrier.

* * * * *